United States Patent [19]

Najer et al.

[11] 4,242,343
[45] Dec. 30, 1980

[54] PHENYLPIPERAZINE DERIVATIVES

[75] Inventors: Henry Najer, Paris; Philippe Manoury, Le Plessis-Robinson, both of France

[73] Assignee: Synthelabo, Paris, France

[21] Appl. No.: 48,814

[22] Filed: Jun. 15, 1979

[30] Foreign Application Priority Data

Jun. 20, 1978 [FR] France .................. 78 18351

[51] Int. Cl.³ .................. A61K 31/495; C07D 405/06; C07D 295/08
[52] U.S. Cl. .................................. 424/250; 544/374; 544/392; 544/394
[58] Field of Search .............. 544/392, 374, 394; 424/250

[56] References Cited

U.S. PATENT DOCUMENTS

| | | | |
|---|---|---|---|
| 2,836,594 | 5/1958 | Parcell | 544/394 |
| 3,089,819 | 5/1963 | Short | 544/394 |
| 3,929,792 | 12/1975 | Bouchara | 544/394 |
| 3,954,763 | 5/1976 | Giudicelli et al. | 544/392 |

*Primary Examiner*—Paul M. Coughlan, Jr.

*Attorney, Agent, or Firm*—Stevens, Davis, Miller & Mosher

[57] ABSTRACT

Phenylpiperazine derivatives corresponding to the formula (I)

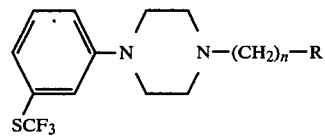

in which n is 1, 2 or 3 and R represents the tetrahydrofuryl-2 radical, or the radical $CH_2$-SH, or a radical $CH_2$-S-alkyl, or a radical $CH_2$-O-alkyl or a radical $CH_2$-S-CO-alkyl, the alkyls having from 1 to 8 carbon atoms, and also their addition salts with pharmaceutically acceptable acids.

These compounds are tranquilizers with psychotropic properties which permit their use in anxiety and depression.

5 Claims, No Drawings

PHENYLPIPERAZINE DERIVATIVES

DESCRIPTION

The present invention relates to phenylpiperazine derivatives, their addition salts with pharmaceutically acceptable acids, their preparation and their application in therapy.

The compounds of the invention correspond to the formula

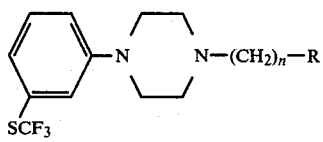
(I)

in which n is 1, 2 or 3 and R represents the tetrahydrofuryl-2 radical or the radical $CH_2$-SH, or a radical $CH_2$-S-alkyl, or a radical $CH_2$-O-alkyl or a radical $CH_2$-S-CO-alkyl, the alkyls having from 1 to 8 carbon atoms.

The addition salts formed by the compounds (I) with pharmaceutically acceptable acids form part of the invention.

According to the invention, the compounds (I) can be prepared by reacting (m-trifluoromethylthio-phenyl)-piperazine (II)

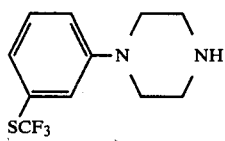

with a compound (III)

Y—(CH$_2$)$_n$—R    (III)

in which R and n have the meanings given above and Y represents an anion of an activated alcohol derivative, such as a halide, mesylate, tosylate or halogenomethanesulphonate ion.

This reaction is carried out at a temperature of 20° to 150° C. in a polar or non-polar solvent such as a benzene hydrocarbon, a hydroxylic or ketonic solvent, dimethylformamide (DMF) or hexamethylphosphorotriamide (HMPT).

In order to prepare the compound in which R is the radical $CH_2SH$, it is also possible to react the phenylpiperazine (II) with ethylene sulphide.

It is also possible to prepare the compounds (I) in which R is

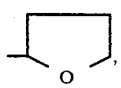

$CH_2O$-alkyl or $CH_2S$-alkyl by reacting the compound (IV)

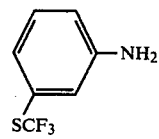

with a compound (V) of the formula

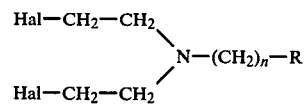

The derivatives (I) in which R is a radical $CH_2$-S-alkyl or $CH_2$-S-CO-alkyl can also be obtained, according to the invention, from the compound (I) of the formula

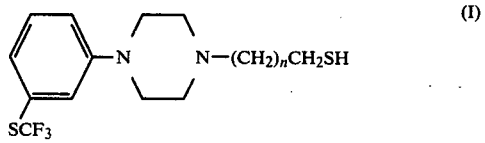
(I)

by reaction with an alkyl halide or with a corresponding acyl halide.

The compounds (III) are described in the literature.

The following examples illustrate the preparation of the compounds of the invention.

The analyses and the IR and NMR spectra confirm the structure of the compounds.

EXAMPLE 1

1-(m-Trifluoromethylthio-phenyl)-4-(tetrahydrofuryl-2-methyl)-piperazine and its hydrochloride.

$$\left[ n = 1, R = \underset{O}{\underline{\phantom{xxxx}}} \right]$$

A mixture of 13.5 g (0.05 mol) of (m-trifluoromethylthio-phenyl)-piperazine, 13.5 g (0.054 mol) of tetrahydrofuryl-2-methyl tosylate and 13.5 ml of HMPT is heated at 120° C. for 2 hours. The mixture is cooled to 10° C. and 100 ml of water are added. The oil is separated from the water and then washed 3 times with water in order to remove the HMPT. The oil is taken up in chloroform, the traces of water are separated off and the chloroform solution is dried over magnesium sulphate. A solution of hydrogen chloride in ether is added and the solvents are evaporated off. The evaporation residue is triturated with ether and the precipitate is filtered off. It is rendered alkaline with 2 N NaOH solution and the mixture is extracted with chloroform. The chloroform is evaporated off and the hydrochloride is prepared from the oil remaining after evaporation. The compound is recrystallised from a mixture of isopropanol and ether.

Melting point = 210° C.

EXAMPLE 2

1-(m-trifluoromethylthio-phenyl)-4-(2-mercaptoethyl)-piperazine and its hydrochloride.

[n=1, R=CH₂SH]

In an Erlenmeyer flask, 3.84 g (0.064 mol) of ethylene sulphide are added dropwise, at 20° C., to a solution of 15 g (0.0557 mol) of (m-trifluoromethylthio-phenyl)-piperazine and 2 ml of methanol.

The mixture is heated gradually to 55° C. and this temperature is maintained for 1 hour 30 minutes. The solvent is evaporated off and the residue is rectified in a bulbed tube.

Boiling point=200° C. under a pressure of 0.1 mmHg.

The hydrochloride is prepared by adding a solution of hydrogen chloride in ether to a solution of the base in ethyl acetate.

Melting point=141° C.

EXAMPLE 3

1-(m-trifluoromethylthio-phenyl)-4-(2-methylthioethyl)-piperazine and its hydrochloride.

[n=1, R=CH₃SCH₂]

0.84 g (0.0175 mol) of a 50% strength dispersion of sodium hydride is added in portions to a solution cooled to +5° C., of 4.8. g (0.015 mol) of 1-(m-trifluoromethylthio-phenyl)-4-(2-mercaptoethyl)-piperazine in 40 ml of DMF. When the evolution of hydrogen has ceased, a solution of 2.16 g (0.0152 mol) of methyl iodide in 20 ml of DMF is added dropwise. The reactants are left in contact overnight. The mixture is poured into ice and the resulting mixture is extracted twice with ether. The ether solution is dried over magnesium sulphate and evaporated.

The hydrochloride is prepared in ethyl acetate by adding the theoretical amount of a solution of hydrogen chloride in ethanol.

Melting point=135° C.

The following table (I) shows the compounds of the invention which have been prepared by way of examples.

TABLE

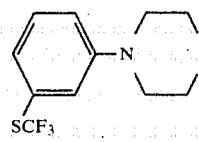

| Compound | n | R | Characteristics of the hydrochloride. Melting point (°C.) |
|---|---|---|---|
| 1 (Example 1) | 1 | ⟨furyl-O⟩ | 210 |
| 2 (Example 2) | 1 | —CH₂SH | 141 |
| 3 (Example 3) | 1 | —CH₂SCH₃ | 135 |
| 4 | 1 | —CH₂—OCH₃ | 151 |

TABLE-continued

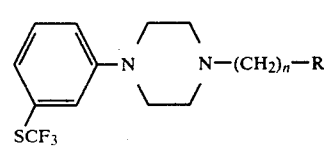

| Compound | n | R | Characteristics of the hydrochloride. Melting point (°C.) |
|---|---|---|---|
| 5 | 1 | —CH₂—S—COCH₃ | 168 |
| 6 | 1 | —CH₂—O—C₄H₉ | 140 |

The compounds of the invention are active in therapy in the field of the central nervous system.

This activity has been demonstrated and measured by the 4 plate test (C. Aron, Thesis in Medicine, Paris 1970; J. R. Boissier, P. Simon and C. Aron, Une nouvelle méthode de détermination des tranquillisants chez la souris ("A new method for testing tranquillisers in mice") Eur. J. Pharmacol. 1968, 4, 145–151).

The compounds are administered orally in several doses (1,3 and 10 mg/kg), 60 minutes before the test. The percentage of disinhibition in the mice is measured.

At a dose of 1 mg/kg, the percentage varies from 35 to 70; at a dose of 3 mg/kg, it varies from 80 to 150 and at a dose of 10 mg/kg, it varies from 120 to 300.

For the same doses, the higher the percentage, the greater is the activity of the compound.

The acute toxicity (LD₅₀) is determined on mice either by intraperitoneal administration after 48 hours or by oral administration for 7 days. The LD₅₀ for intraperitoneal administration varies from 75 to 230 mg/kg. The LD₅₀ for oral administration varies from 250 to 1,000 mg/kg.

The compounds of the invention possess psychotropic properties which permit their use for the treatment of various states of anxiety and of depression.

They can be administered orally or parenterally with any suitable excipient in any suitable form of administration, namely sugar-coated pills, tablets, capsules, dragees, injectable solutions and the like.

The daily posology can range from 5 to 200 mg.

We claim:

1. Phenylpiperazine derivatives corresponding to the formula (I)

in which n is 1,2 or 3 and R represents the tetrahydrofuryl-2 radical, or the radical CH₂-SH, or a radical CH₂-S-alkyl, or a radical CH₂-O-alkyl or a radical CH₂-S-CO-alkyl, the alkyls having from 1 to 8 carbon atoms, and also their addition salts with pharmaceutically acceptable acids.

2. Derivatives according to claim 1, in which n is equal to 1 and R is a radical CH₂SH, CH₂S-alkyl, CH₂-O-alkyl or CH₂SCO-alkyl.

3. Derivatives according to claim 2, in which the alkyl is the methyl radical.

4. A compound according to claim 1, which is 1-(m-trifluoromethylthio-phenyl)-4-(2-tetrahydrofurylmethyl) piperazine.

5. A pharmaceutical composition which contains a compound as specified in claim 1 in an effective tranquilizing dosage.

* * * * *